(12) United States Patent
Matsuno

(10) Patent No.: US 6,795,572 B1
(45) Date of Patent: Sep. 21, 2004

(54) IMAGE PROCESSING APPARATUS

(75) Inventor: Hiroyuki Matsuno, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 595 days.

(21) Appl. No.: 09/631,127

(22) Filed: Aug. 2, 2000

(30) Foreign Application Priority Data

Aug. 3, 1999 (JP) .......................................... 11-220468

(51) Int. Cl.[7] .............................................. G06K 9/00
(52) U.S. Cl. .................... 382/132; 382/254; 382/312
(58) Field of Search ................................. 382/309, 318, 382/319, 132, 254; 250/363.09; 358/406, 523; 348/262

(56) References Cited

U.S. PATENT DOCUMENTS

| | | | |
|---|---|---|---|
| 4,916,640 | * 4/1990 | Gasperi et al. | 382/291 |
| 5,400,792 | * 3/1995 | Hoebel et al. | 378/115 |
| 5,606,632 | * 2/1997 | Matsumoto et al. | 382/298 |
| 5,644,610 | * 7/1997 | Crawford et al. | 378/19 |

* cited by examiner

Primary Examiner—Amelia M. Au
Assistant Examiner—Colin LaRose
(74) Attorney, Agent, or Firm—Fitzpatrick, Cella, Harper & Scinto

(57) ABSTRACT

The invention provides an image processing apparatus capable of continuing the image capture operation without correction error, even in the absence of the correcting condition corresponding to the configuration of a sensor unit connected to a control unit. For this purpose, there are provided memory means for storing the ID information for identifying the selected sensor, memory means for storing the correction table corresponding to the ID information, and search means for searching the correction table corresponding to the ID information, and, in the absence of the correcting condition for the configuration of the connected sensor unit, there is searched substitute correcting information and the image processing is executed with the later determined correcting information.

11 Claims, 13 Drawing Sheets

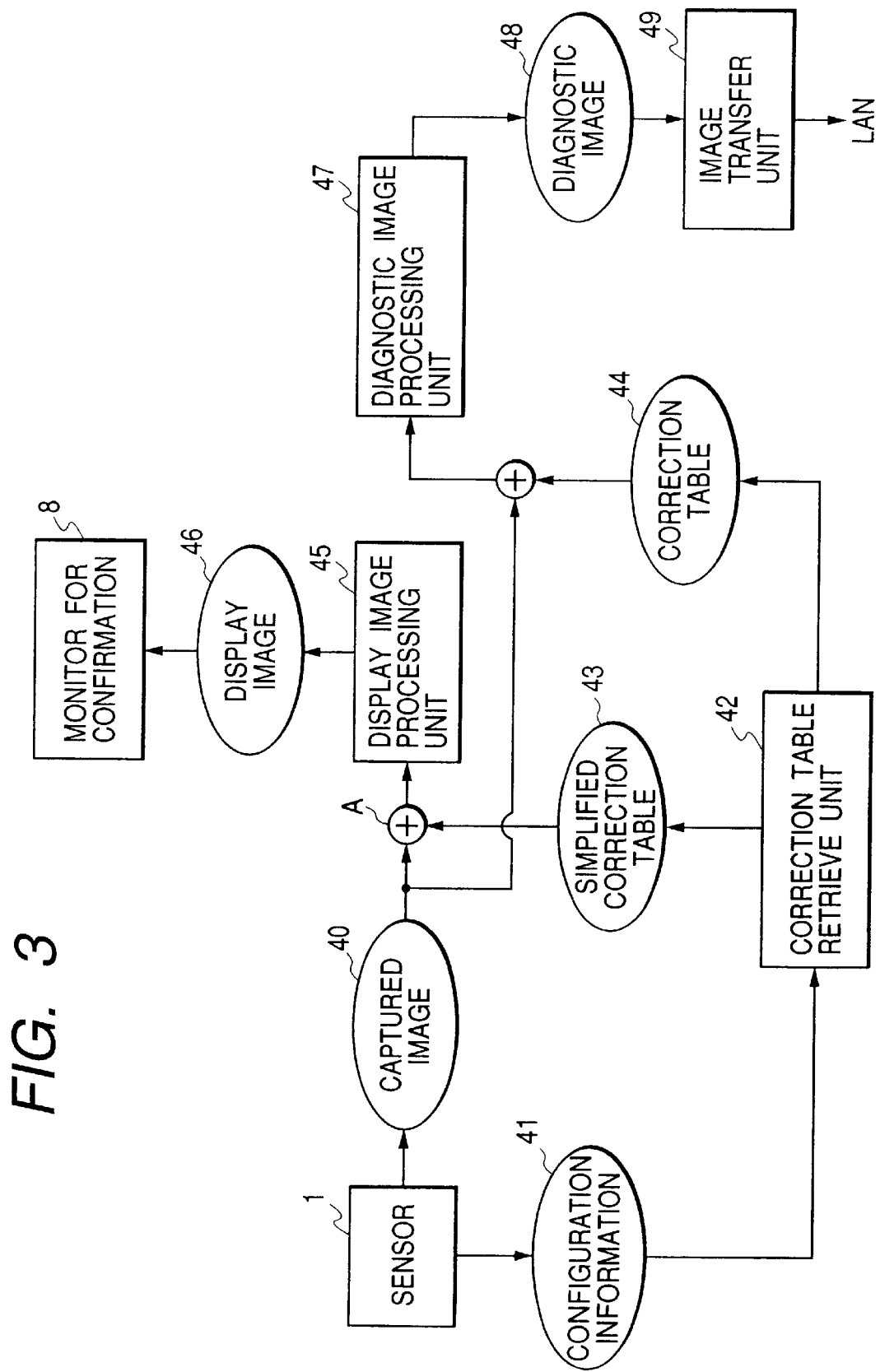

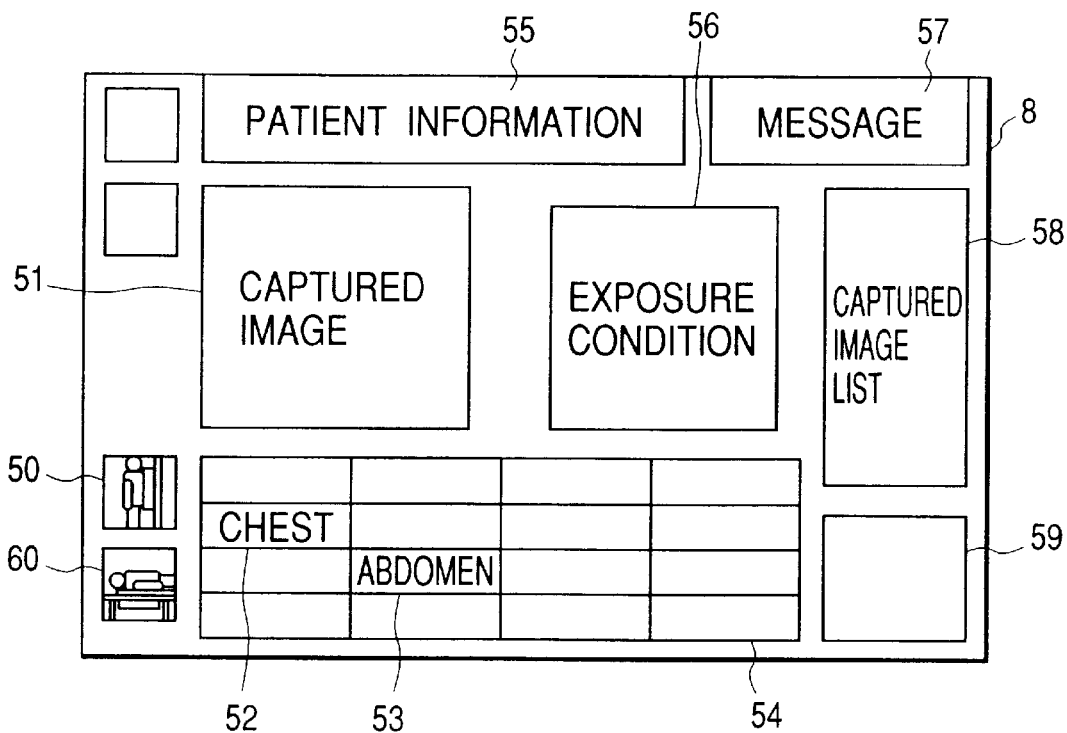
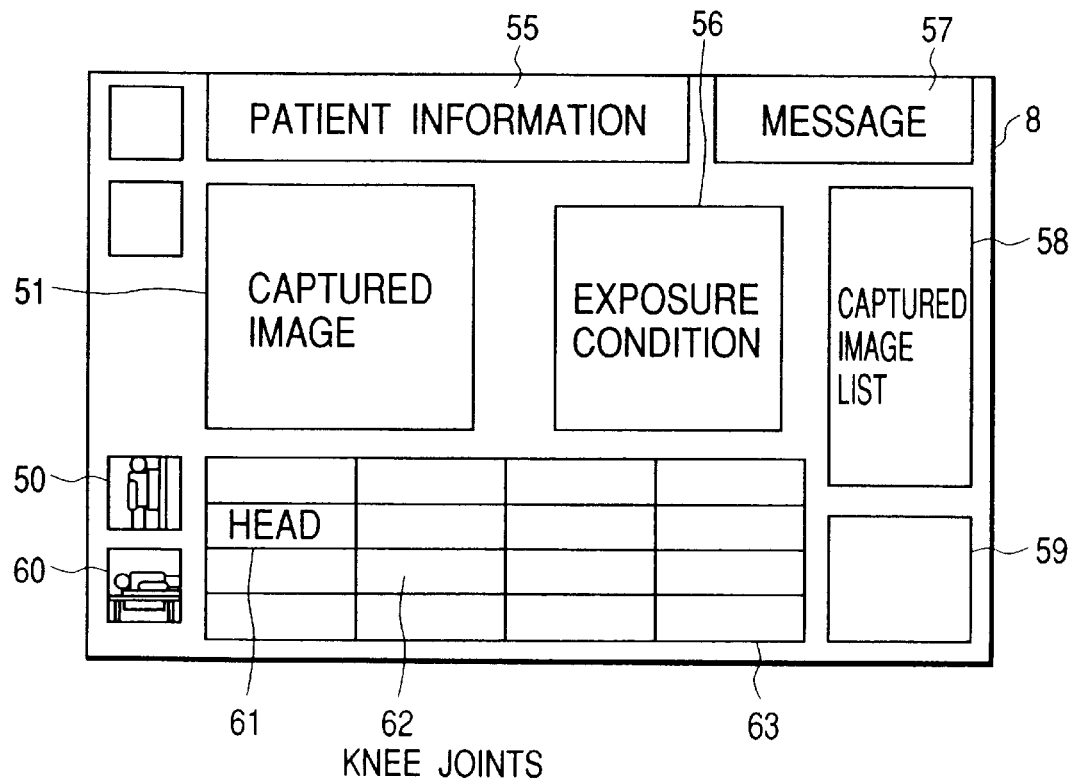

FIG. 6

| SENSOR SERIAL NUMBER | KIND OF FLUORESCENT SUBSTANCE | KIND OF GRID | PHOTO -TIMER | CORRECTION TABLE | |
|---|---|---|---|---|---|
| 10011 | 0001 | 1 | 1 | white10011. 111<br>defPix10011. 111 | ~501 |
| 10012 | 0001 | 0 | 1 | — | ~502 |
| 10012 | 0001 | 1 | 1 | white10012. 111<br>defPix10012. 111 | ~503 |
| 10012 | 0001 | 1 | 0 | white10012. 110<br>defPix10012. 111 | ~504 |
| 10012 | 0002 | 1 | 1 | white10012. 211<br>defPix10012. 211 | ~505 |
| 10045 | 0001 | 0 | 1 | white10100. 201<br>defPix10100. 201 | ~506 |

FIG. 7

| SENSOR SERIAL NUMBER | KIND OF FLUORESCENT SUBSTANCE | KIND OF GRID | PHOTO -TIMER | CORRECTION TABLE | |
|---|---|---|---|---|---|
| 10011 | 0001 | 1 | 1 | white10011. 111<br>defPix10011. 111 | ~501 |
| 10012 | 0001 | 0 | 1 | white10012. 101<br>defPix10012. 101 | ~502 |
| 10012 | 0001 | 1 | 1 | white10012. 111<br>defPix10012. 111 | ~503 |
| 10012 | 0001 | 1 | 0 | white10012. 110<br>defPix10012. 111 | ~504 |
| 10012 | 0002 | 1 | 1 | white10012. 211<br>defPix10012. 211 | ~505 |
| 10045 | 0001 | 0 | 1 | white10100. 201<br>defPix10100. 201 | ~506 |

FIG. 8

| SENSOR SERIAL NUMBER | LOT NUMBER |
|---|---|
| 000001—000010 | 0001 |
| 000011—000023 | 0002 |
| 010001—010046 | 0003 |
| 010100—010199 | 0004 |

| SENSOR SERIAL NUMBER | LOT NUMBER |
|---|---|
| 000001—000010 | 0001 |
| 000011—000013 | 0002 |
| 010001—010046 | 0003 |
| 010100—010199 | 0004 |
| 010200—010299 | 0005 |

| SENSOR SERIAL NUMBER | KIND OF FLUORESCENT SUBSTANCE | KIND OF GRID | PHOTO-TIMER | CORRECTION TABLE |
|---|---|---|---|---|
| 10011 | 0001 | 1 | 1 | white10011. 111<br>defPix10011. 111 |
| 10012 | 0001 | 0 | 1 | — |
| 10012 | 0001 | 1 | 1 | white10012. 111<br>defPix10012. 111 |
| 10012 | 0001 | 1 | 0 | white10012. 110<br>defPix10012. 111 |
| 10012 | 0002 | 1 | 1 | white10012. 211<br>defPix10012. 211 |
| 10010 | 0001 | 0 | 1 | white10100. 201<br>defPix10100. 201 |

| SENSOR SERIAL NUMBER | KIND OF FLUORESCENT SUBSTANCE | KIND OF GRID | PHOTO-TIMER | CORRECTION TABLE |
|---|---|---|---|---|
| 10011 | 0001 | 1 | 1 | white10011. 111<br>defPix10011. 111 |
| 10012 | 0001 | 0 | 1 | — |
| 10012 | 0001 | 1 | 1 | white10012. 111<br>defPix10012. 111 |
| 10012 | 0001 | 1 | 0 | white10012. 110<br>defPix10012. 111 |
| 10012 | 0002 | 1 | 1 | white10012. 211<br>defPix10012. 211 |

~604

IMAGE PROCESSING APPARATUS

BACKGROUND OF THE INVENTION

1. Field of the Invention

The present invention relates to the processing of image data obtained, for example, by X-ray imaging.

2. Related Background Art

For X-ray image sensing for medical diagnosis, there has conventionally been employed a film-screen system in which a fluorescent screen and an X-ray photographic film are combined. In this method, X-rays being transmitted through an object are amplified according to the intensity thereof by the fluorescent screen and irradiate the X-ray photographic film, thereby forming an X-ray image showing information of the interior of the object.

Recently there has been introduced a digital X-ray image sensing apparatus in which X-rays converted by a fluorescent substance into visible light proportional to the intensity thereof, and such visible light is converted by a photoelectric converting element into an electrical signal and further converted into a digital signal by an A/D converter. For such photoelectric converting element there is being used amorphous silicon, which, in comparison with the digital X-ray image sensing apparatus utilizing the conventional image intensifier, allows one to form a large, thin and light sensor unit, and thereby an image sensing mode as in the conventional film-screen system is made possible.

Also, in the conventional X-ray image sensing room, the equipment includes a Bucky unit for mounting a cassette containing the film and the screen. Such a unit is available in a stand type for sensing the X-ray image of the patient in the standing position and a table type for sensing the X-ray image of the patient in the lying position, and plural units are often provided in a single X-ray image sensing room.

Also, the X-ray image sensing room is often equipped with plural X-ray generating bulbs, but only one of such plural sensor units is used for irradiation since only one patient at a time is subjected to image sensing.

In such digital X-ray image sensing systems, it is required to use a control unit and an operation unit in common and to execute the image sensing by switching between the plural sensor units.

On the other hand, the X-ray sensor unit of a cassette type can be carried manually and connected to various control portions, so that an X-ray sensor unit can be used in turn in different X-ray image sensing rooms.

However, each X-ray sensor unit has its own characteristics for the digital image sensing.

For example, the solid-state image pickup device in the X-ray sensor unit usually has 2700×2700 pixels, and certain defects in such pixels are inevitable. For this reason the pixel defect information, indicating the defective pixels, is important and the image has to be corrected according to such information before being used for diagnosis.

Also, as the sensitivity characteristics are different from pixel to pixel, the charge amount accumulated for a same amount of light fluctuates. Such fluctuation is corrected by gain correction, which is executed according to a correction table indicating the normalized output under the uniform irradiation of X-rays. The image sensing for preparing such gain correction table is called calibration imaging.

Also, in each X-ray sensor unit, the correcting conditions vary according to the image sensing method because the detachable grid, the fluorescent substance, the phototimer, etc., are changed, so that the correction process in the control unit also varies. The information of these conditions has to be entered into the control unit each time the digital X-ray sensor unit connected to the control unit is changed, and the calibration imaging has to be conducted each time. These operations are very cumbersome to the user. Also, the calibration imaging may become necessary in the course of the X-ray image sensing operation, and the waiting time of the patient becomes very long in such case.

SUMMARY OF THE INVENTION

The object of the present invention is to execute optimum image processing according to the sensor unit.

The above-mentioned object can be attained, according to aspect of the present invention, by providing an image processing apparatus that has an X-ray irradiation unit which irradiates X-rays, one or more X-ray sensor units each of which includes an X-ray sensor which converts the X-rays into an electric signal, selection means for selecting the X-ray sensor units, information obtaining means for obtaining information for a sensing environment, memory means for storing correction data corresponding to the information for the sensing environment, and correction means for correcting outputs of the X-ray sensor units using the correction data corresponding to the information obtained by the information obtaining means. In a case in which the memory means does not contain correction data corresponding to the information obtained by the information obtaining means, the correction means selects the correction data from among the correction data stored in the memory means, on the basis of one of either a serial number of the X-ray sensor or a lot number of the X-ray sensor, to effect the correction using the selected correction data.

According to another aspect of the present invention, there is also provided a control method for an image processing apparatus including memory means storing plural correction data respectively corresponding to plural sensor units, each containing a sensor for sensing the image of an object, the method including selecting the X-ray sensor units, obtaining the information for the sensing environment, and in a case in which the memory means does not contain correction data corresponding to the obtained information, selecting from among the correction data stored in the memory means, either a serial number of the X-ray sensor or a lot number of the X-ray sensor, to effect correction using the selected correction data.

According to another aspect of the present invention, there are also provided a memory medium storing a program for controlling an image processing apparatus according to the mentioned method, and a program for performing such control.

Other objects of the present invention, and the features thereof, will become fully apparent from the following description which is to be taken in conjunction with the accompanying drawings. Moreover, while additional features of the present invention are disclosed herein, the present inventor does not waive any portion of what he has disclosed.

BRIEF DESCRIPTION OF THE DRAWINGS

FIG. 3 is a functional block diagram showing an image processing step in the medical X-ray image sensing system of the first embodiment of the present invention;

FIGS. 4 and 5 are views showing examples of the image display in the medical X-ray image sensing system of the first embodiment of the present invention;

FIGS. 6 and 7 are conceptual views showing examples of a correction table in the medical X-ray image sensing system of the first embodiment of the present invention;

FIGS. 8 and 9 are conceptual views showing examples of lot data in the medical X-ray image sensing system in a second embodiment of the present invention;

FIGS. 10 and 11 are conceptual views showing examples of a correction table in the medical X-ray image sensing system of the second embodiment of the present invention;

DESCRIPTION OF THE PREFERRED EMBODIMENTS

In the following, the present invention will be explained in detail by reference to the preferred embodiments thereof.

Figure 2:
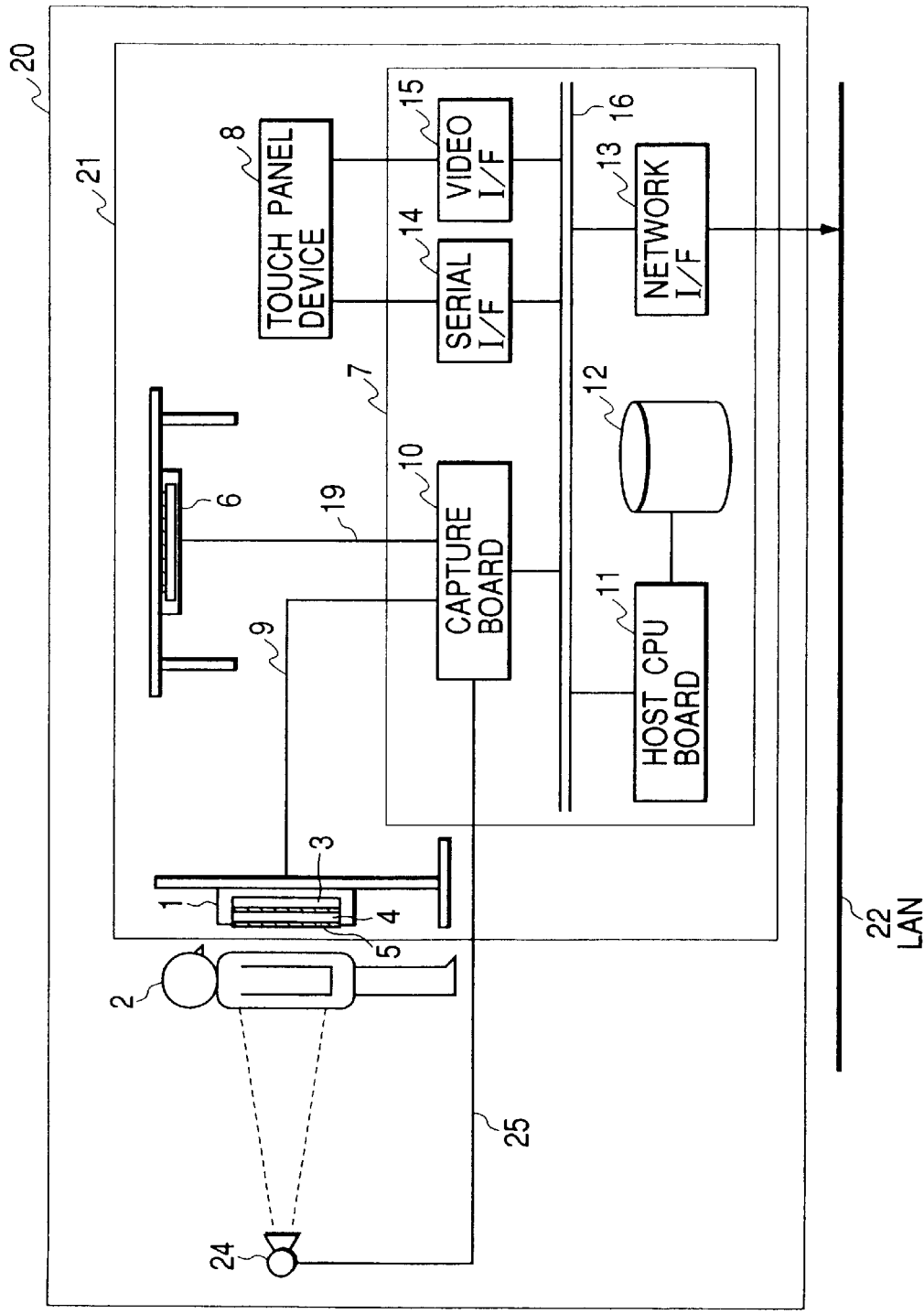
FIG. 2 is a block diagram showing the entire configuration of the medical X-ray image sensing system of the first embodiment of the present invention.

FIG. 2 is a system block diagram of a hospital X-ray image sensing room according to a first embodiment of the present invention.

A medical digital X-ray image sensing system 21 having flat sensor units is provided with a stand position sensor unit 1 and a lying position sensor unit 6, each containing a large area sensor 3, and is further provided with sub systems such as a control unit 7 for synchronizing the exposure between an X-ray generation apparatus 24 and the sensor units 1, 6, and for executing image acquisition and image processing of the sensed image, and a touch panel device 8 constituting the user interface (I/F) with the operator. The stand position sensor unit 1 is provided with a grid 5, a fluorescent substance 4, a photoelectric converting device 3, etc. There is also shown a patient 2.

The stand position sensor unit 1 and a capture board 10 for accumulating the sensed image data are connected through a data line 9 which is used for power supply, image transfer and control signal transfer, while the lying position sensor unit 6 and the capture board 10 are connected through a data line 19.

An image generated by a program functioning on a host CPU board 11 is displayed on the touch panel device 8 constituting the user I/F, through a video I/F 15.

FIG. 4 shows an example of the image displayed on the touch panel device 8.

A doctor or a technician who is the user of the present digital X-ray image sensing system operates the system by actuating buttons displayed on the image. More specifically, coordinate data corresponding to a depressed button is transferred to the host CPU board 11, by a program functioning thereon, through a serial I/F 14, and, based on such information, the host CPU board 11 executes a process corresponding to the depressed button. The process relating to FIG. 4 will be explained later again.

Referring to FIG. 2, a hard disk 12 serves to store the program which functions on the host CPU board 11, and also serves to temporarily store various correction information required for the image sensing and the sensed image. There are also provided a PCI bus 16, which is an internal bus of the control unit 7, a network I/F 13 for transferring the sensed image to an external equipment through a LAN 22, and an X-ray I/F 25 connecting the control unit 7 and the X-ray generation apparatus 24.

Figure 1:
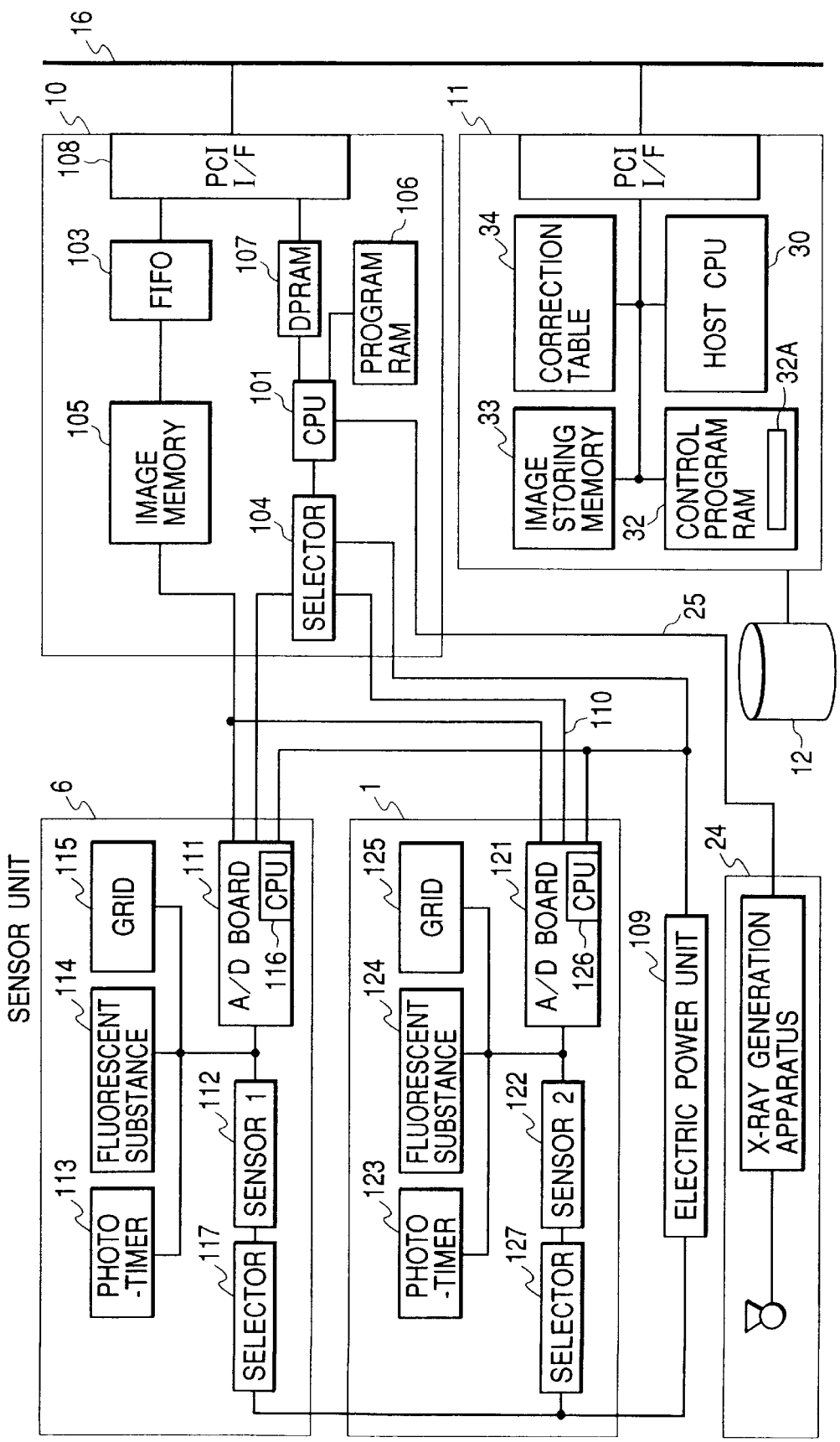
FIG. 1 is a block diagram showing the configuration of a medical X-ray image sensing system constituting a first embodiment of the present invention.

FIG. 1 shows an example of the configuration of the host CPU board 11, capture board 10 and sensor units 1, 6 in the X-ray image sensing unit 21.

The host CPU board 11 is provided with a host CPU 30. The present embodiment employs a Pentium® processor as the host CPU 30 and Windows NT® as the operating system (both being trade names). A control program RAM 32 is provided for causing the function of the control program, a control program 32A read from the hard disk 12 functions on the control program RAM 32. There are also provided an image storing memory 33 for storing the sensed image transferred from the sensor units 1, 6, and a correction table memory 34 storing a correction table for correcting the sensed image.

Also, the capture board 10 is provided with a sub-CPU 101 which executes the timing control of the X-rays, since the synchronization required with the X-ray generation apparatus 24 on the order of several milliseconds cannot be ensured on the Windows NT® program functioning on the host CPU 30. Such timing control is executed through the X-ray I/F 25, and the sensed image is once transferred to an image memory 105 and is transferred, in response to a command from the host CPU 30, from a PCI I/F 108 through a FIFO 103. The communication between the host CPU 30 and the sub-CPU 101 is executed by writing and reading commands, determined by the program, into or from a DPRAM 107. The program of the sub-CPU 101 functions on the program RAM 106.

The sensor unit 6 is provided with an A/D board 111 having the sub-CPU 116, a photo-timer 113, a fluorescent substance 114, a grid 115, a first sensor 112 and a selector 117. The sensor unit 1 has a similar configuration and is provided with an A/D board 121 having a sub-CPU 126, a photo-timer 123, a fluorescent substance 124, a grid 125, a second sensor 122 and a selector 127.

There are also provided a power supply unit 109, and a signal line 110 connecting the sensor units 1, 6 with the capture board 10.

FIG. 3 shows an example of the processing step for the image data sensed for example with the sensor unit 1.

When the sensor unit 1 is connected to the control unit 7 shown in FIG. 2, the configuration information 41 of the sensor unit 1, for example the serial number of the sensor, kind of the fluorescent substance and the grid, etc., are transferred from the sensor unit 1 to the control unit 7. According to the configuration information 41, the control unit 7 causes correction table searching means 42 to search correction tables, thereby acquiring correction table information 44 consisting of a gain correction table, defect correcting information, etc., and simplified correction table information 43 for executing simplified correction. In response to the X-ray exposure by the X-ray generation apparatus 24, there are obtained sensed image data 40, sensed by the sensor unit 1. The sensed image data 40 are processed by display image processing means 45, utilizing the aforementioned correction table information 43, 44, whereby a confirmation image 46 is displayed on the touch panel device 8 serving also as a confirming monitor.

When the examination of the patient is completed by repeating the image acquisition as explained in the foregoing, the examination information is renewed and the sensed image data 40 are processed by diagnostic image process means 47 to obtain a diagnostic image 48. The prepared diagnostic image 48 is transferred, by image transfer means 49, to an external image display device or a medical printer through a LAN, thereby being used for diagnosis.

FIG. 4 shows an example of the image configuration of the touch panel device 8 constituting the user I/F in the present X-ray image sensing system 21.

There are provided an area 55 for displaying patient information entered from a magnetic card (not shown) or the touch panel device 8; an area 51 for displaying the captured X-ray image; an area 56 for displaying the entered exposure conditions; an area 54 for positioning buttons for instructing the setting of image sensing parameters defining the body position to be sensed (for example a chest button 52, an abdomen button 53, etc.); an area 58 for displaying the captured images as a list; an area 59 for a button for entering completion of image sensing; a button 50 for selecting the stand position sensor unit; and a button 60 for selecting the lying position sensor unit.

In the following there will be explained the actual method of use, with reference to FIGS. 4 and 1.

For example in case of chest image sensing of the patient 2, the user at first enters the information of the object patient, such as name, birth date, sex, etc., into the control unit 7 utilizing a magnetic card reader or the like. In a case in which the patient has forgotten the magnetic card, a keyboard is displayed for example on the image of the touch panel device 8, and various information are entered from such keyboard.

Then the user depresses for example the button 50 for selecting the stand position sensor unit 1, whereby the host CPU 30 sends a selection signal to the sub-CPU 101 and turns on the power supply for the stand position sensor unit 1 through the selector 104. The stand position sensor unit is for example a type in which the grid 5 cannot be replaced and the replacement of the fluorescent substance 4 is not easy for the user, so that the sub-CPU 126 in the sensor unit 1 always sends fixed configuration information such as "sensor serial number 10011, fluorescent substance type 1, grid type 1, photo timer present" to the host CPU 30.

Then the host CPU 30 searches a condition for correcting the current sensor unit on the hard disk 12 serving as the correction table memory. The hard disk 12 stores, for example, ID information and correction tables as shown by items 501 to 505 in FIG. 6. In the present example, the item 501 matches the condition. Thus, gain correction data "white 10011. 111" and defect pixel data "defPix 10011. 111" are read from the database 12 and are loaded in the correction table memory 34. The means for holding the serial number of the sensor unit can be a flush memory capable of holding the data regardless whether the power supply is turned on or not, or DIP switches to be set at the shipment from the manufacturer.

Then, for determining the image processing condition for the sensed image, the user selects the button 52 for selecting the chest as the image sensing object, from the button registration tray 54. The button 52 is linked by the program with the image sensing method, image processing condition, correction table for the chest, and the control unit 7 also fetches exposure information such as the bulb voltage, bulb current, exposure time, etc. and transfers these information to the sub-CPU 101.

After the above-mentioned preparation, the user sets the patient in a proper position and depresses the exposure button of the X-ray generation apparatus 24. The X-ray generation apparatus 24 and the control unit 17 are synchronized through the X-ray I/F 25, and the X-ray emitted from the X-ray generation apparatus 24 is transmitted by the patient 2 and enters the sensor unit 1. The entering X-rays, containing the internal information of the patient 2, are subjected to the interception of scattered X-ray by the grid 5, and then are converted by the fluorescent substance 4 into visible light proportional to the intensity of X-ray, and a charge proportional to the intensity of the visible light is accumulated in the photoelectric conversion device 3. The accumulated charge is digitized by A/D conversion and is transferred to the capture board 10 in the control unit 7. The transferred image data are temporarily stored in the image memory 105, and are then transferred to the image memory 33 of the host CPU board 11. The image data are then subjected, in the host CPU 30, to image processing according to the program and are displayed as a confirmation image on the touch panel device 8.

In the following there will be explained a case of abdomen image sensing with the stand position sensor unit 1.

As the stand position sensor unit 1 is already selected, the user depresses the button 53 corresponding to the abdomen image sensing condition. Since a longer exposure time is generally selected for the abdomen image sensing than in the chest image sensing, the sub-CPU 101 makes a setting for reducing the moving speed of the grid. Also, there is employed a correction table same as that for the chest image sensing.

Now there will be explained a case requiring the lying position sensor unit 6 for a third image, for example a case of head image sensing.

In this case, the user selects, on the touch panel device 8, the button 60 for selecting the lying position sensor unit. In response, the display on the touch panel device 8 is switched to an image for lying position image sensing as shown in FIG. 5, and the display of the buttons for selecting the image sensing positions is switched to that 63 for lying position image sensing, including a head button 61 and a knee joint button 62. Also a message display column 57 displays a message such as "Sensor being switched. Please wait.", and, in the meantime, an instruction for switching the sensor unit is transmitted from the host CPU 30 through the DPRAM 107 to the sub-CPU 101 of the capture board 10 whereupon the sub-CPU 101 initiates a disconnecting process for the stand position sensor unit 1. When the disconnection of the stand position sensor unit 1 becomes possible, the sub-CPU 101 receives a halt signal from the sub-CPU 126, whereby the selector 104 executes power supply control to turn off the power supply to the stand position sensor unit 11.

Then the power supply of the lying position sensor unit 6, instructed for connection, is turned on. In response, the sub-CPU 116 in the sensor unit 6 sends the sensor information such as the serial number, fluorescent substance type, grid type, presence/absence of photo-timer, etc., of the sensor equipped in the sensor unit 6, to the host CPU 30. In the present example, for example, the host CPU 30 acquires information as to "serial number 10012, fluorescent substance type 1, grid 1, photo timer present". Then the host CPU 30 searches the correction table memory to find the item 503 shown in FIG. 6. Thus, gain correction data "white 10012, 111" and defect pixel data "defPix 10012, 111" are read and are loaded in the correction table memory 34.

When the switching of the correction information is completed, the message column 57 on the touch panel device 8 displays a message "Select the image sensing method". The user, wishing the head image sensing, depressed the button 61 representing "head", and then executes the X-ray image sensing in a similar manner as explained in the foregoing.

In the following there will be explained a case of knee joint image sensing as a fourth image.

Figure 13:
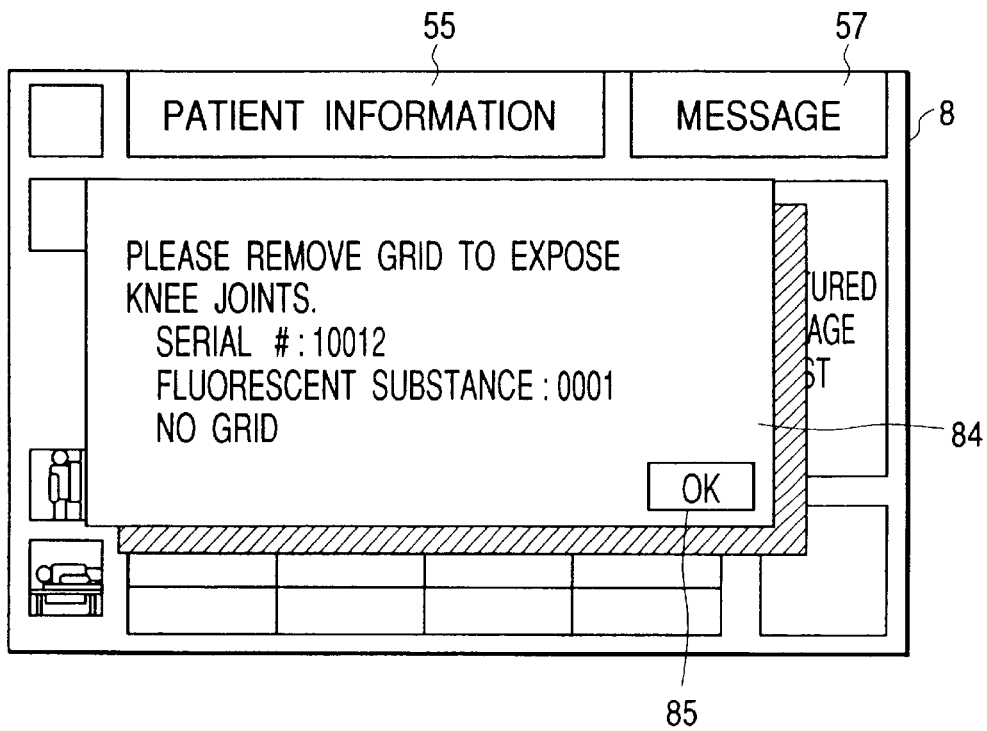

Since the grid is not used for the knee joint image sensing, an image sensing with the grid of the configuration employed in the head image sensing does not match the data linked with the image sensing method. Therefore, an error display 84 as shown in FIG. 13 is executed, requesting the removal of the grid by the user. Understanding the message, the user depresses an OK button 85. Otherwise, the exchange of the grid as required for the image sensing may be automatically executed by a grid changer mechanism.

Then the user depresses the button 60 for selecting the lying position sensor unit on the touch panel device 8, whereupon the CPU 101 of the capture board 10 initiates the disconnection process for the lying position sensor unit 6. When the disconnection of the sensor unit 6 becomes possible, there is received a halt signal, whereby the capture board 10 executes power supply control to turn off the power supply to the sensor unit 6. Then the user detaches the grid from the sensor unit 6, and depresses again the button 60 for instructing the connection of the lying position sensor unit. In response, the capture board 10 turns on the power supply to the lying position sensor unit, and the sub CPU 116 in the sensor unit 6 sends the information such as the serial number, fluorescent substance type, grid type, presence/absence of photo timer, etc., of the sensor equipped in the sensor unit 6, to the host CPU 30. In the present example, for example, there is transmitted information of "serial number 10012, fluorescent substance type 1, grid 0, and photo-timer present". "Grid 0" means absence of the grid.

Then the host CPU 30 searches the condition for correcting the current configuration of the sensor unit, on the hard disk 12 constituting the correction table memory. In this case, if a correction table for the absence of the grid is not present as indicated by the item 502 in FIG. 6, an error display 81 is made on the image of the touch panel device 8 as shown in FIG. 12.

Figure 12:
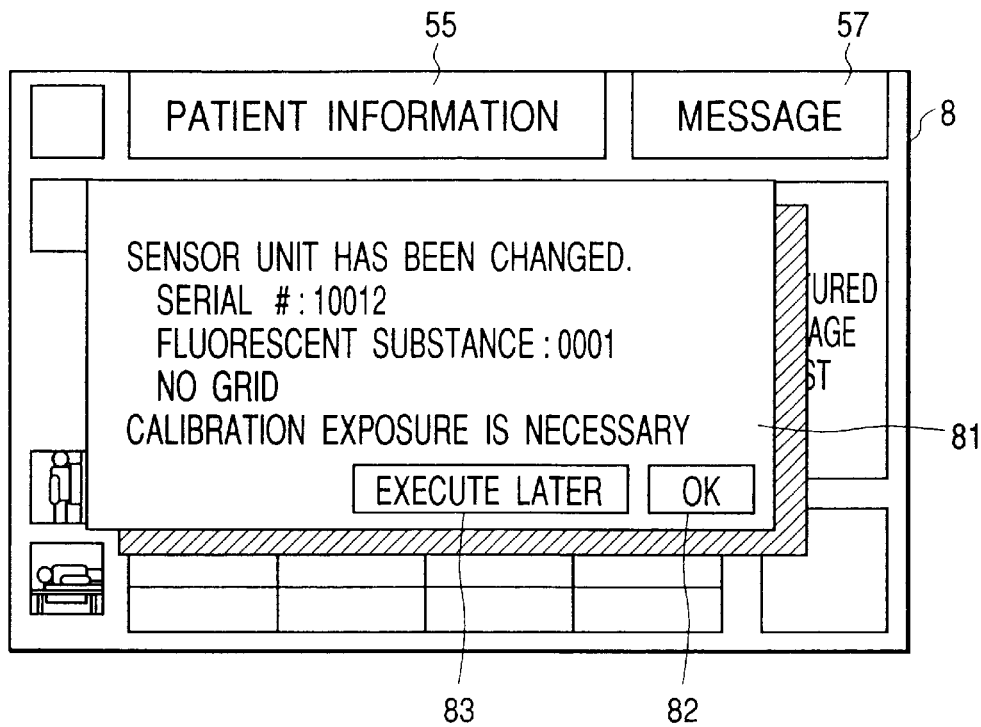
FIGS. 12, 13 and 14 are views showing examples of image display in the medical X-ray image sensing system of the first embodiment of the present invention.

The above-described situation is usually not encountered since the correction data for the combination of the sensor units based on the image sensing method are prepared by the service personnel, but, if the correction table is not prepared or if a grid of unrecommended kind is mounted in the sensor unit, the sequence enters a state for waiting for an input by the user as shown in FIG. 12, which is an error state in which the continuation of the image sensing operation is disabled. A similar error state is encountered in case the sensor unit is exchanged in the course of the image sensing operation and the corresponding correction table cannot be found.

Figure 14:
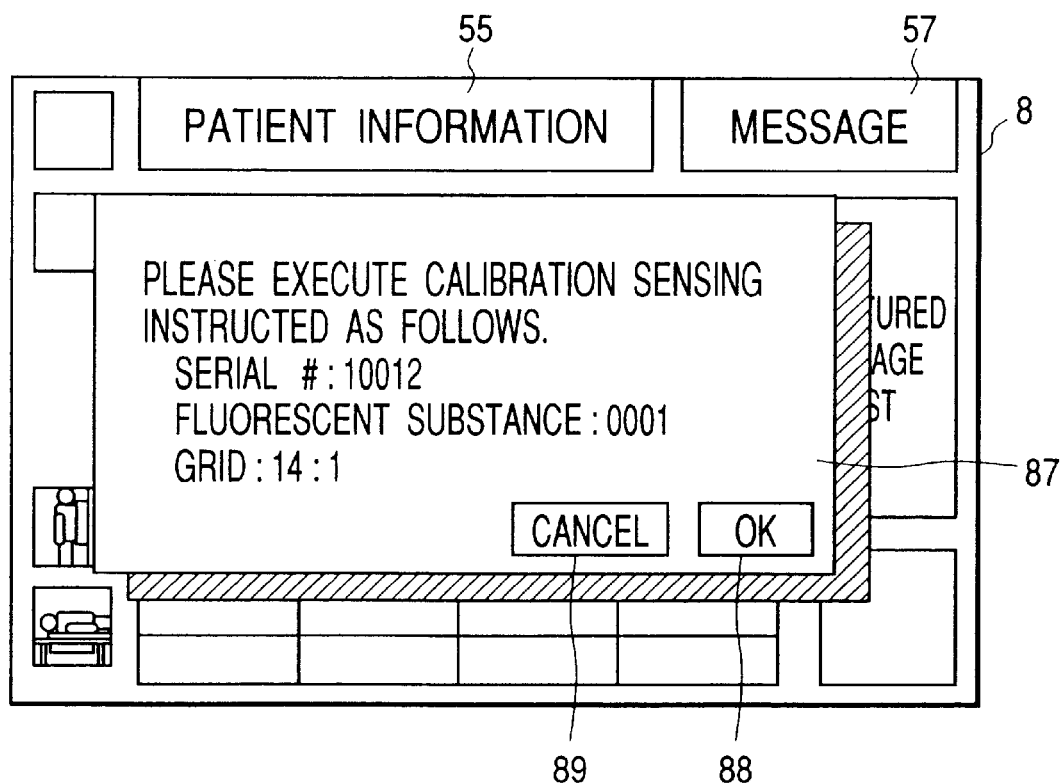

In such situation, the user can continue the ordinary image sensing operation by executing registration in the item 502 of the correction table, as shown in FIG. 7, by depressing the OK button 82 and executing calibration. FIG. 14 shows an example 87 of the image display requesting execution of the calibration. The user depresses the OK button 88 in case of executing the calibration, but depresses the cancel button 89 in case of not executing the calibration.

It is not practical, however, to execute the calibration imaging and to prepare the correction table on the spot while the patient is waiting for the image sensing, since such operations cause the patient to wait for a long time. Therefore, as shown in FIG. 12, there is depressed a setting button 83 for executing the calibration imaging later, thereby adopting a scheduling of executing the calibration after the image sensing of the patient.

In such case, it is necessary to confirm, by the display image, whether the image sensing of the patient is successful. Therefore, search means searches a substitute correction table from a database containing the correction tables. It is desirable to use a correction table corresponding to the true sensor unit, but the display image prepared with the substitute correction table provides little influence because the image for confirmation is only used for confirming that the image sensing is successful and does not require a definition as high as that of the diagnostic image.

If the display image is not corrected by a substitute correction table, a correction error will appear on the captured image as artifact, and then the user can not confirm the image sensing.

After the image sensing of the patient, the display image is corrected with the substitute correction table and is confirmed by the user on the display monitor, and the patient is released if the examination is completed by confirming the successful image sensing. However, for the processing of the diagnostic image, it is necessary to acquire the true correction table for image processing.

After the completion of examination, the image processing is initiated, but the correction process constituting a part of the diagnostic image processing 47 cannot be executed if the aforementioned correction information is contained in the information associated with the sensed image. Therefore the necessary scheduled correction information is acquired by a calibration image sensing and the image processing is completed with such correction information.

In the foregoing embodiment there has been explained a case with two sensors, but, in case the configuration is changed even in a single sensor unit, it is effective to detect such change in the configuration and to automatically change the correcting condition. Though it is possible, at the starting of the control unit 7, to search whether the correction tables are provided in the memory for all the image sensing methods for the connected sensor units, and to cause the user to execute the necessary calibration image sensing, the aforementioned correction table error is evidently encountered in case the sensor unit is detached and replaced in the course of image sensing of the patient, and the aforementioned method of the present embodiment for temporarily continuing the image sensing operation with the substitute correction table is effective.

Also, the present invention can naturally be implemented by means of using a memory medium storing the program codes of software realizing the functions of the aforementioned embodiments in a system or an apparatus, where a CPU of such system or apparatus reads and executes the program codes stored in the memory medium. In such case the program codes themselves of the software read from the memory medium realize the novel functions of the invention, and the memory medium storing the program codes constitutes an embodiment of the present invention. The memory medium for supplying the control program 32A is not only the control program RAM 32 but also a ROM (not shown), or a separate memory medium such as a floppy disk, a hard disk, an optical disk, a magnetooptical disk, a CD-ROM or a non-volatile memory card. Also, the functions of the aforementioned embodiments are realized not only in a case where the computer executes the read program codes but also in a case where an operating system or the like functioning on the computer executes all or a part of the actual processes under the control of such program codes. Further, the present invention is naturally applicable to a case where program codes of software realizing the functions of the aforementioned embodiments are delivered, from a memory medium storing such program codes, to the user through a communication line for example by personal computer communication.

Figure 15:
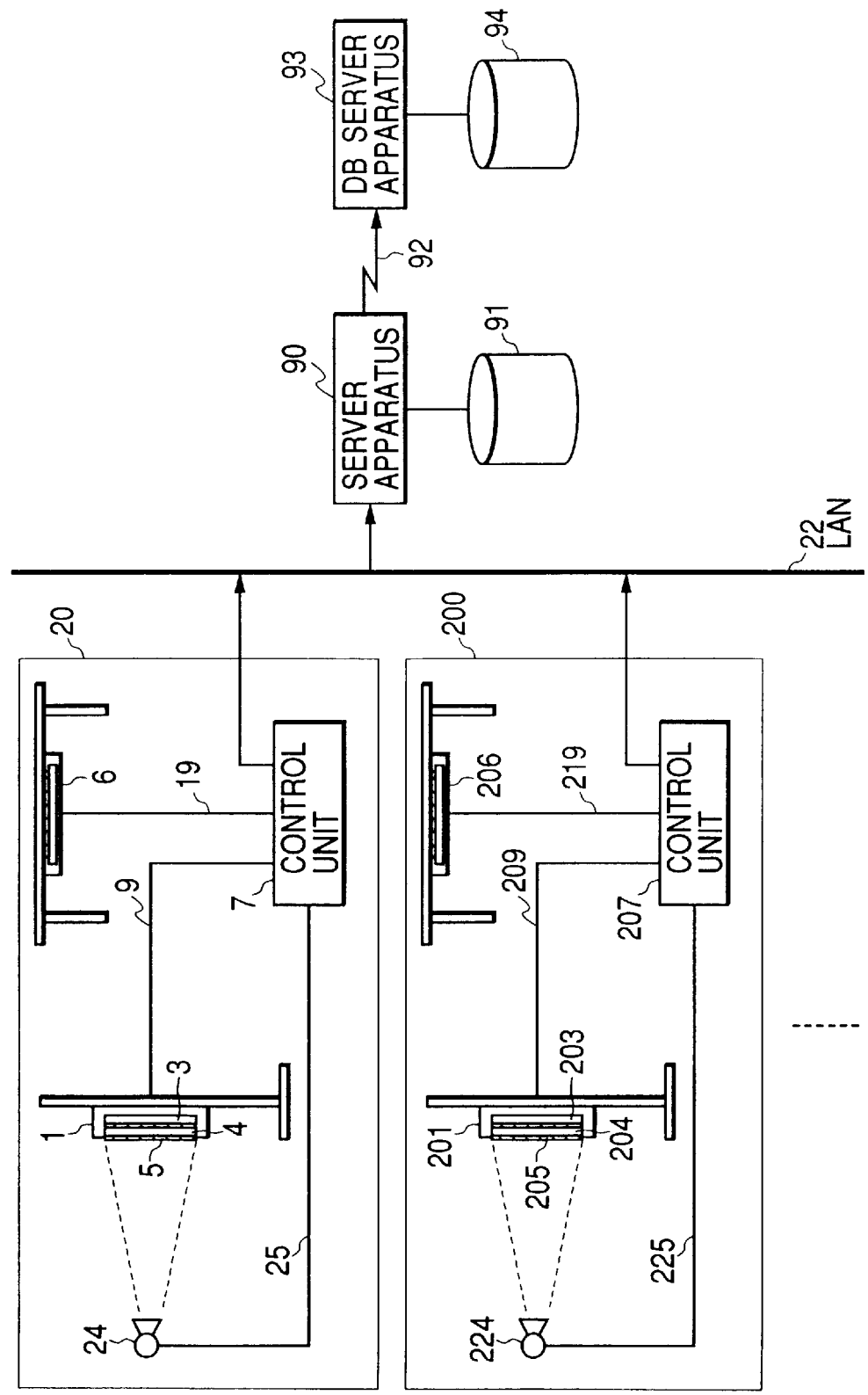
FIG. 15 is a block diagram showing the entire configuration of the medical X-ray image sensing system of the second embodiment.

FIG. 15 shows a second embodiment of the present invention.

In the image sensing room 20 of the aforementioned first embodiment, it is possible to detach the sensor unit 6 from the Bucky table and to connect it to a control unit 207, different from the control unit 7, in another image sensing room 200. The control unit 207, to which the sensor unit 6 is connected instead of the lying position sensor unit 206, reads the configuration information specific to the sensor unit 6 and searches the correction information therefor in the correction table memory of the control unit 207, but such correction information cannot be acquired since it is stored in the control unit 7.

In FIG. 15, there are shown a stand position sensor unit 201, a photoelectric converting device 203, a fluorescent substance 204, a grid 205, data lines 209, 210, an X-ray generating device 224 and an X-ray I/F 225.

In the present second embodiment, therefore, the correction table information is managed by a server 90 on a LAN 22.

In the following there will be explained, with reference to FIG. 16, an example of control by the host CPU of the control unit for acquiring the correction table utilizing the control program.

At first, in a step S100, the control unit acquires the ID information of the sensor unit when it is connected to the control unit. Then a step S101 causes the user to select the image sensing method, and a step S102 searches the correction table of such ID information, as will be explained in details with reference to FIG. 17. Then a step S103 executes image acquisition, and a step S104 executes display image processing. In the preparation of the display image, there is used the correction information acquired in the step S103. Then, in a step S105, the user executes confirmation by the display image, and, if the image sensing is successful, the sequence proceeds to a step S106. If the image sensing failed for example by a movement of the patient, the sequence returns to the step S103 for executing the image sensing again. Then, if a step S106 identifies that the image sensing is to be executed on another body part of the patient, the sequence returns to the step S100. If the user depresses an examination end button in the step S106, the sequence proceeds to a step S107 for executing an examination end process such as renewing the examination information.

Then the image processing is initiated. At first, a step S108 checks a substitute correction flag associated with the object of image sensing, and, if the flag is on, the sequence proceeds to a step S111 for executing a calibration image sensing. Then a next step S112 prepares a correction table and the sequence proceeds to the step S109. In case the step S108 identifies that the flag is off, the sequence directly proceeds to the step S109 for executing diagnostic image processing. Then a step S110 executes a process for transfer to an external equipment.

Figure 17:
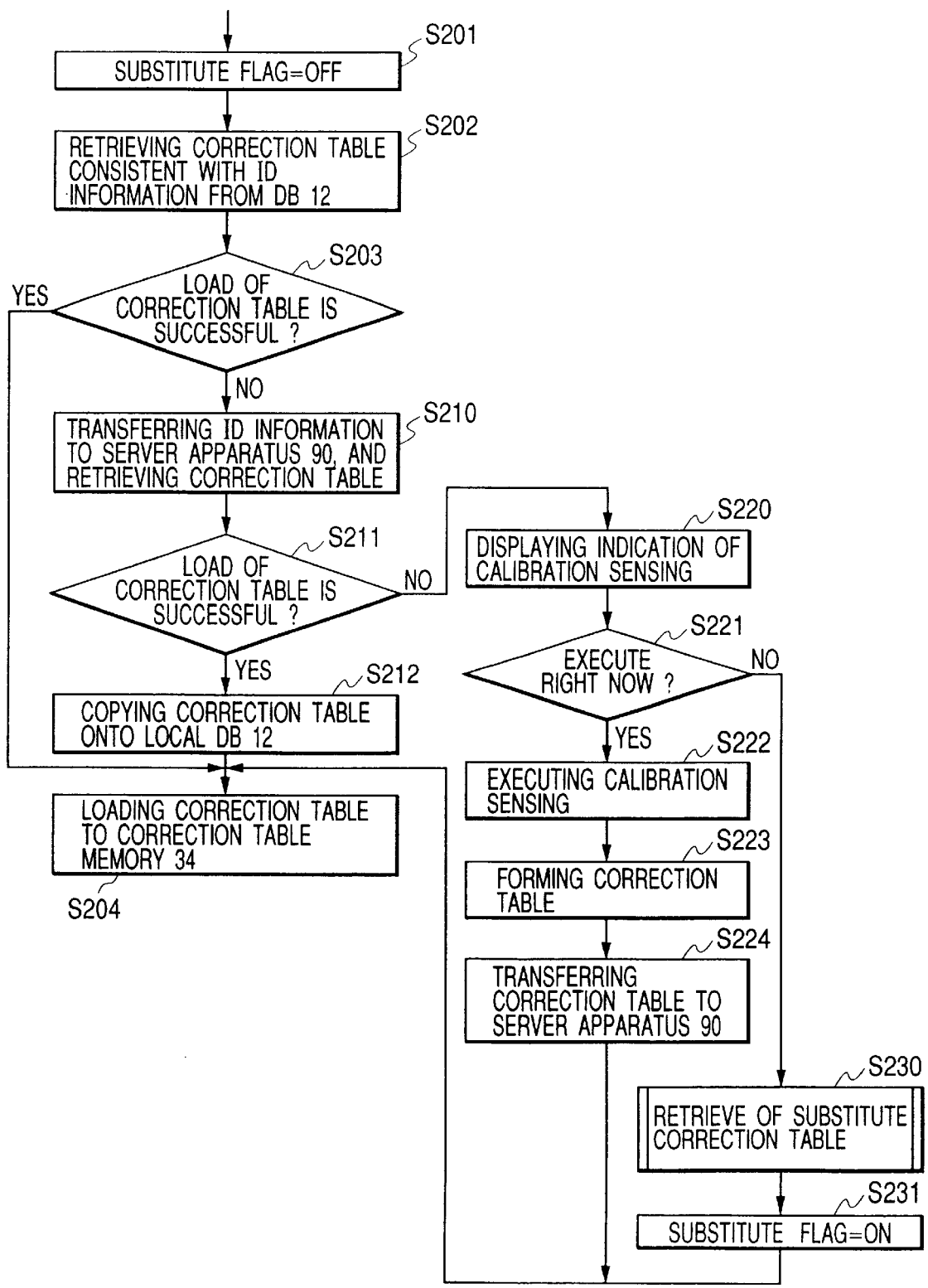

In the following there will be explained the correction table search process, with reference to FIG. 17.

At first a step S201 initializes the substitute correction table flag, associated with the image sensing object, to the off state. Then a step S202 searches the correction table corresponding to the configuration ID information of the aforementioned sensor unit, from a local correction information memory (for example the hard disk 12 in FIG. 2). Then, if a step S203 identifies that the search in the step S202 is successful, the sequence proceeds to a step S204 for transferring the loaded correction table to a correction table memory 34 (cf. FIG. 1) in preparation for the image sensing.

On the other hand, if the step S203 identifies the failure of the search, the sequence proceeds to a step S210 for transferring the ID information to the server 90 for the purpose of enquiry for the presence of the correction information by the client means. The server 90 executes search in the correction table memory 91, and, if the correction information is found in a step S211, the correction information is transferred from the server 90 and the sequence proceeds to a step S212. In the step S212, the client means causes a local correction information memory 12 to store the correction table.

On the other hand, if the step S211 identifies the absence of the correction table, the sequence proceeds to a step S220 for requesting the calibration image sensing to the user as in the foregoing first embodiment shown in FIG. 12. If a next step S221 identifies that the calibration image sensing is to be immediately executed, the sequence proceeds to a step S222 for executing the calibration image sensing. Then a next step S223 normalizes the calibration data and prepares the gain correction table and the defect correction table. Then a step S224 causes the client means to transfer the newly acquired correction table in order to register it in the server 90. After the above-described process, the sequence proceeds to the step S204 for loading the correction table, prepared on the control unit, in the correction table memory 34.

The server 90 need not necessarily be an independent device but can be constituted by a control unit of an X-ray image sensing system, provided on the LAN. Furthermore, such server need not be present on the LAN but can be composed of a master database server present on the internet 92. A numeral 94 indicates a correction table memory of such master database server 93.

Figure 18:
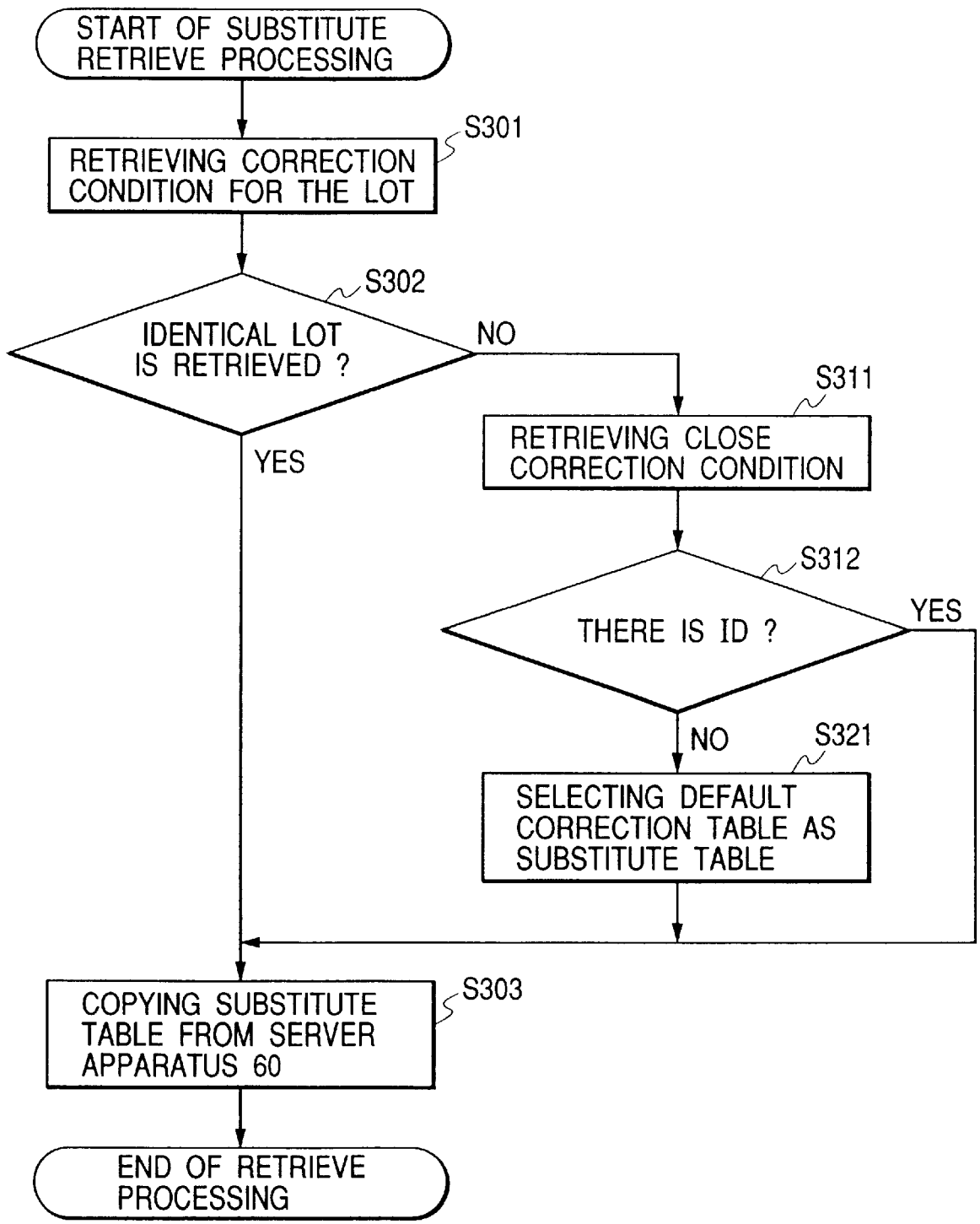

If the aforementioned step S221 identifies that the calibration image sensing is scheduled to be executed later, the sequence proceeds to a step S230 for searching a substitute correction table, as will be explained later in relation to FIG. 18. When the substitute correction table is acquired, a next step S231 sets the substitute correction flag, associated with the image sensing object, to the on state, whereby the image sensing operation is continued with the substitute correction table.

In the following there will be explained a search process for the substitute correction table, with reference to FIG. 18.

At first a step S301 searches a sensor of a same lot. The sensors of a particular manufacturing lot, having been produced by the same manufacturing process, have similar output characteristics of the sensor panel. In a size-reduced image used for confirming display image, the error resulting from the fluctuation between the sensors can be absorbed because the pixels are averaged. The lot data are stored in the hard disk 12 in a format shown in FIG. 8, and can be easily renewed by replacement of the lot data as indicated by 602 in FIG. 9, when the sensor units of a new lot are produced.

For example, in the fourth image sensing in the foregoing first embodiment, since the configuration information is "sensor serial number 10012, fluorescent type 1, grid 0, photo timer present", there are searched sensor serial numbers belonging to the lot 3 as indicated in the item 601 in FIG. 8, and there is selected, as the substitute, the correction information of a sensor having configuration information "sensor serial number 10045, fluorescent type 1, grid 0, photo timer present", indicated in the item 506 in FIG. 6. Though the sensor of the serial number 10012 has other correction tables, but there is no correction table without grid. Therefore, the correction with other correction data may show stripe pattern of the grid, and the correction information of the sensor of the serial number 10045 is more preferable.

In a case in which the correction information of the same lot is not present as shown in FIG. 10, the sequence proceeds from the step S302 to a step S311 in which is selected the correction information 603 which has a similar correcting condition while the manufacturing lot is different. Also, in a case where the search condition is not met as shown in FIG. 11, the sequence proceeds to a step S321 for selecting the correction information 604 as a default condition for executing the display image processing, though a correction error such as a stripe pattern is anticipated.

Figure 16:
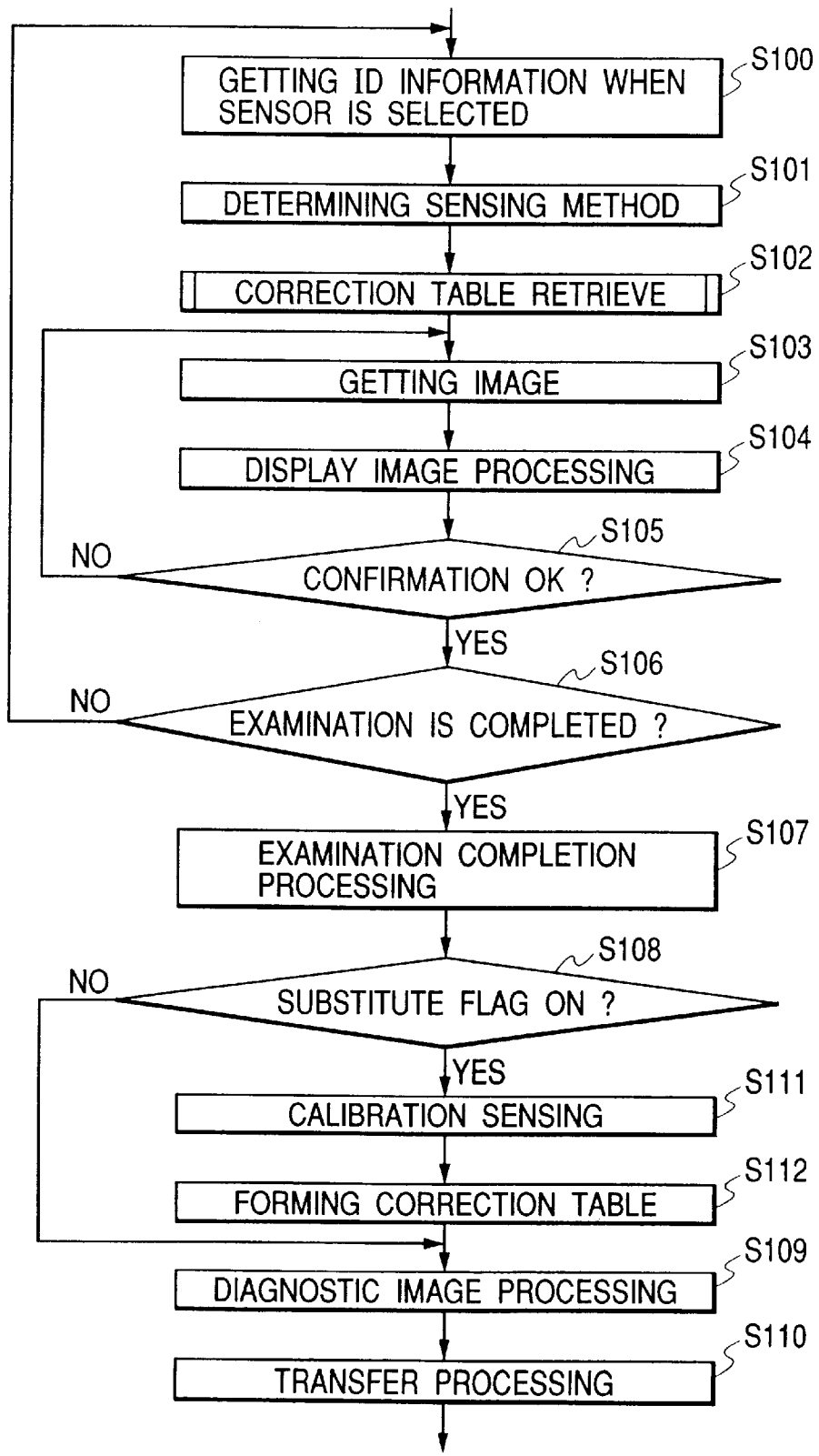
FIGS. 16, 17 and 18 are flow charts showing the correction control flow in the medical X-ray image sensing system of the second embodiment.

In the present substitute process, the scheduled calibration image sensing is executed in the step S111 in FIG. 16. As a result, as indicated by an item 502 in FIG. 7, the correction table can be registered in the correction table memory and can be used for the diagnostic image processing. It can also be used as the normal correction information or as the substitute correction information in the succeeding image sensing operations.

In an environment where the sensor configuration is switched, as explained in the foregoing, the correction information is switched in response to the instruction of the user for switching, but the image sensing operation cannot be continued in the absence of such correction information. In the present invention, even if the calibration is not yet completed, a substitute correction table is searched and temporarily used thereby enabling to complete the image sensing operation for the patient and to execute the calibration later, whereby the image sensing operation can be executed efficiently.

Many widely different embodiments of the present invention may be constructed without departing from the spirit and scope of the present invention. It should be understood that the present invention is not limited to the specific embodiments described in the specification, except as defined in the appended claims.

What is claimed is:

1. An image processing apparatus comprising:

an X-ray irradiation unit which irradiates X-rays;

one or more X-ray sensor units each of which includes an X-ray sensor which converts the X-rays into an electric signal;

selection means for selecting the X-ray sensor units;

information obtaining means for obtaining information for a sensing environment;

memory means for storing correction data corresponding to the information for the sensing environment; and correction means for correcting outputs of said X-ray sensor units using the correction data corresponding to the information obtained by said information obtaining means, wherein, in a case in which said memory means does not have stored therein correction data corresponding to the information obtained by said information obtaining means, said correction means selects the correction data from among the correction data stored in said memory means, on the basis of one of a serial number of the X-ray sensor and a lot number of the X-ray sensor, to effect the correction using the selected correction data.

2. An image processing apparatus according to claim 1, further comprising image display means for displaying data corrected by said correction means.

3. An image processing apparatus according to claim 1, wherein the sensing environment includes at least one of a kind of a fluorescent material, kind of a grid, presence/absence of the grid, and presence/absence of a photo-timer.

4. An image processing apparatus according to claim 3, wherein said information obtaining means obtains the information for the sensing environment from output information of the X-ray sensor unit selected by said selection means.

5. An image processing apparatus according to claim 1, wherein the sensing environment includes at least one of a sensing condition, a part to be sensed, and a sensing method.

6. An image processing apparatus according to claim 5, wherein said information obtaining means includes information inputting means and obtains the information for the sensing environment from the input information.

7. An image processing apparatus according to claim 1, wherein the correction data comprise at least one of gain correction table and defect correction information.

8. An image processing apparatus according to claim 1, wherein said memory is arranged on a network which is a LAN or Internet.

9. A control method for an image processing apparatus provided with an X-ray irradiation unit which irradiates X-rays, one or more X-ray sensor units each of which includes an X-ray sensor which converts the X-rays into an electric signal, and memory means for storing correction data corresponding to information for a sensing environment, said control method comprising the steps of:

selecting the X-ray sensor units;

obtaining the information for the sensing environment; and in a case in which the memory means does not have stored therein correction data corresponding to the information obtained in said information obtaining step, selecting, from among the correction data stored in the memory means, one of a serial number of the X-ray sensor and a lot number of the X-ray sensor, to effect correction using the selected correction data.

10. A computer-readable recording medium which stores thereon a program for executing a control method for an image processing apparatus provided with an X-ray irradiation unit which irradiates X-rays, one or more X-ray sensor units each of which includes an X-ray sensor which converts the X-ray into an electric signal, and memory means for storing correction data corresponding to information for a sensing environment, said control method comprising the steps of:

selecting the X-ray sensor units;

obtaining the information for the sensing environment; and in a case in which the memory means does not have stored therein correction data corresponding to the information obtained in said information obtaining step, selecting, from among the correction data stored in the memory means, on the basis of one of a serial number of the X-ray senor and a lot number of the X-ray sensor, to effect correction using the selected correction data.

11. A program for executing a control method for an image processing apparatus provided with an X-ray irradiation unit which irradiates X-rays, one or more X-ray sensor units each of which includes an X-ray sensor which converts the X-rays into an electric signal, and memory means for storing correction data corresponding to information for a sensing environment, said control method comprising the steps of:

selecting the X-ray sensor units;

obtaining the information for the sensing environment; and in a case in which the memory means does not have stored therein correction data corresponding to the information obtained in said information obtaining step, selecting, from among the correction data stored in the memory means, on the basis of one of a serial number of the X-ray senor and a lot number of the X-ray sensor, to effect correction using the selected correction data.

* * * * *

UNITED STATES PATENT AND TRADEMARK OFFICE
CERTIFICATE OF CORRECTION

PATENT NO.       : 6,795,572 B1
DATED            : September 21, 2004
INVENTOR(S)      : Hirojuki Matsuno It is certified that error appears in the above-identified patent and that said Letters Patent is hereby corrected as shown below:

Column 1,
Line 19, "X-rays converted" should read -- X-rays are converted --.

Column 2,
Line 15, "aspect" should read -- one aspect --.

Column 5,
Line 44, "photo timer" should read -- photo-timer --; and
Line 66, "etc." should read -- etc., -- and "these" should read -- this --.

Column 7,
Line 3, "depressed" should read -- depresses --;
Line 28, "sub CPU 116" should read -- sub-CPU 116 --;
Line 31, "photo timer," should read -- photo-timer, --; and
Line 37, "unit," should read -- unit --.

Column 10,
Line 66, "photo timer" should read -- photo-timer--.

Column 11,
Line 4, "photo timer" should read -- photo-timer --; and
Line 6, "but" should be deleted.

Column 12,
Line 64, "senor" should read -- sensor --.

UNITED STATES PATENT AND TRADEMARK OFFICE
CERTIFICATE OF CORRECTION

PATENT NO. : 6,795,572 B1
DATED : September 21, 2004
INVENTOR(S) : Hirojuki Matsuno It is certified that error appears in the above-identified patent and that said Letters Patent is hereby corrected as shown below:

Column 14,
Line 6, "senor" should read -- sensor --.

Signed and Sealed this

Twenty-fourth Day of January, 2006

JON W. DUDAS
*Director of the United States Patent and Trademark Office*